United States Patent [19]
Hoey et al.

[11] Patent Number: 5,383,873
[45] Date of Patent: Jan. 24, 1995

[54] SMOOTH MUSCLE CHEMICAL PACEMAKER

[75] Inventors: Michael Hoey, Shoreview; Peter Gehlbach, Minneapolis, both of Minn.

[73] Assignee: Regents of the University of Minnesota, Minneapolis, Minn.

[21] Appl. No.: 987,748

[22] Filed: Dec. 9, 1992

[51] Int. Cl.$^6$ .............................................. A61K 9/22
[52] U.S. Cl. .................................. 604/891.1; 128/898; 424/923
[58] Field of Search .................. 604/890.1–892.1, 604/19; 128/898; 424/422–426, 473, 486–490

[56] References Cited

U.S. PATENT DOCUMENTS

| | | | |
|---|---|---|---|
| 4,693,895 | 9/1987 | Wong et al. | 604/892.1 |
| 4,723,958 | 2/1988 | Pope et al. | 604/892.1 |
| 4,747,847 | 5/1988 | Negruder et al. | 604/892.1 |
| 4,777,049 | 10/1988 | Magruder et al. | 604/892.1 |
| 4,878,905 | 11/1989 | Blass | 604/891.1 |
| 4,883,666 | 11/1989 | Sabel et al. | |
| 4,892,538 | 1/1990 | Aebischer et al. | 604/891.1 |
| 4,957,494 | 9/1990 | Wong et al. | 604/891.1 |
| 5,156,844 | 10/1992 | Aebischer et al. | 604/891.1 |

FOREIGN PATENT DOCUMENTS

| | | | |
|---|---|---|---|
| 2178956 | 2/1987 | United Kingdom | 604/890.1 |

OTHER PUBLICATIONS

American Heritage Dictionary (second edition), 1982; pp. 74, 269 and 823.
The Merck Index (tenth edition), 1983, pp. 13, 140, 850, and 1070.
S. K. Sarna et al., *Am. J. Physiol.*, 241:G16–23 (1981).
M. H. Sleisenger and J. S. Fordtran (eds.); *Gastrointestinal Disease: Pathophysiology, Diagnosis, Management*, vol. 11, "Movement of the Small and Large Intestine", 1088–1105 (1989).
C. F. Code (ed.) *Handbook of Physiology*, section 6, vol. IV, "The Alimentary Canal, Motility", p. 2173 only (1968).
P. J. Dzuik and B. Cook, *Endocrin.*, 78:208 (1966).
J. Folkman and V. H. Mark, *Trans. N.Y. Acad. Sci.*, 30:1187 (1968).
E. R. Garrett and P. B. Chemburkar, *J. Pharm. Sci.*, 57:1401 (1968).
F. A. Kincl et al., *Acta. Endo.*, 64:253 (1970).
K. Sundaram and F. A. Kincl, *Steroids*, 12:517 (1968).
H. Tatum, *Contracep.*, 1:253 (1970).
W. E. Berndtson et al., *Endocrin.*, 95:1 (1974).
G. L. Neil et al., *Chemother.*, 18:27 (1973).
J. Folkman and D. M. Long *Ann, N.Y. Acad. Sci.*, 111:857 (1964).
H. Gottlieb et al., *Physiol. and Behavior*, 12:61 (1974).
T. J. Roseman, *J. Pharm. Sci.*, 61:46 (1972).
D. R. Mishell and M. E. Lumkin, *Fert. and Steril.*, 21:99 (1970).
F. Theeuwes et al., *J. Pharm. Sci.*, 63:427 (1974).
William G. Jones et al., *Surgery*, –:63 (Jan. 1990).

*Primary Examiner*—C. Fred Rosenbaum
*Assistant Examiner*—Chalin Smith
*Attorney, Agent, or Firm*—Patterson & Keough

[57] ABSTRACT

Methods and articles of manufacture are provided for treating disorders of smooth muscle function in organ systems. A treatment element comprises a biocompatible polymer matrix loaded with a neuroactive substance. The device is placed in contact with the targeted organ system in a manner effecting a therapeutic effect on the smooth muscle function of the organ system.

17 Claims, 7 Drawing Sheets

PACEMAKER APPLIED

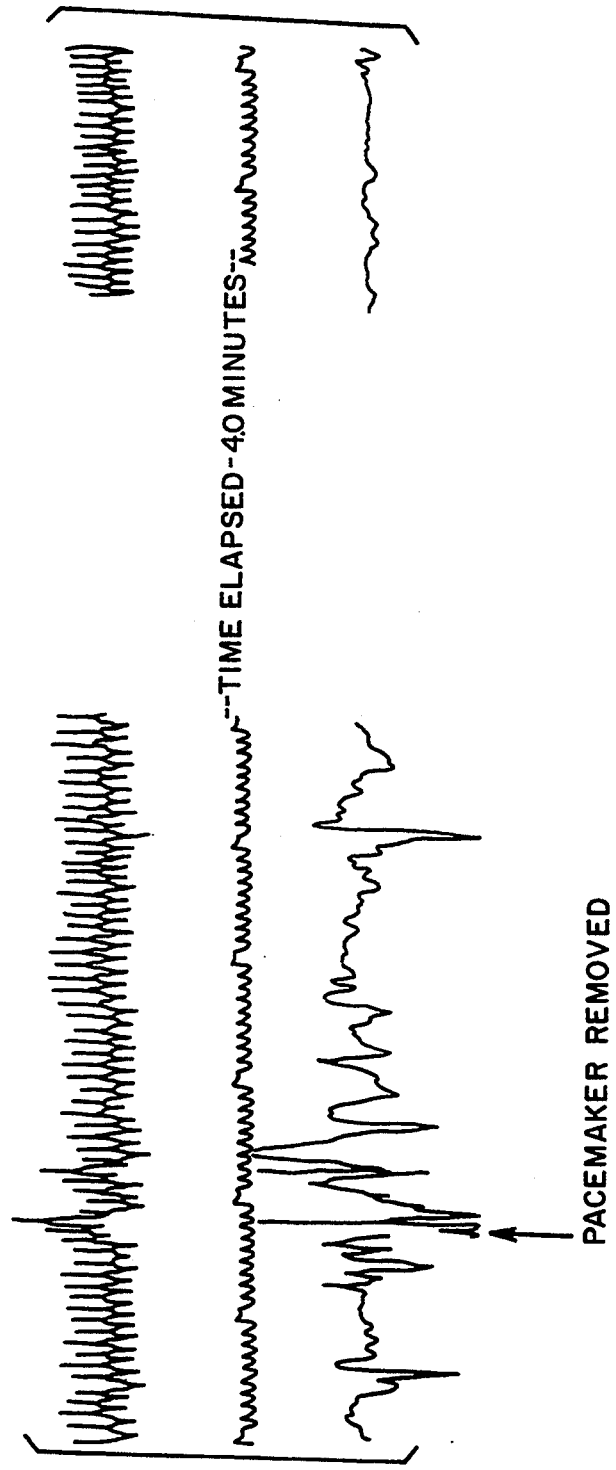

10 SEC.

PACEMAKER APPLIED

SMOOTH MUSCLE CHEMICAL PACEMAKER

FIELD OF THE INVENTION

This invention relates generally to the field of methods for treating disorders associated with smooth muscle function in an organ system. In particular this invention relates to a method and article of manufacture for controlled, localized delivery of at least one neuroactive substance to said organ system having a therapeutic effect on the disorder.

BACKGROUND OF THE INVENTION

A common complication after abdominal surgery and, in some cases chest surgery, is that the patients' intestines immediately post-surgery do not function properly. Such patients are often afflicted with "paralytic ileus" and are at increased risk for emesis, aspiration and secondary pneumonias. They are more prone to surgical complications because they fail to properly empty irritating gastric acid from their stomachs and intestinal fluid from their bowels. For example, wound disruption may occur because of the strain of vomiting the gastric acid. These patients may not be permitted to ingest food for several days after their operations. In such cases, nasogastric intubation is often necessary to achieve adequate gastric emptying. Nourishment cannot be provided by the gastrointestinal route during this period. Wound healing and the immune response are therefore depressed in these patients. Nutrition, if provided, requires intravenous feeding which has its own set of risks.

Nasogastric intubation can be extremely uncomfortable for the patient. Further, the procedure itself can cause medical complications. However, delaying the reinstitution of nutritional support in patients is an undesirable alternative because such patients have an increased metabolic demand while their bodies attempt to heal from surgery. A need clearly exists for a method to efficiently and safely stimulate the gastrointestinal tract such that patients may receive nourishment and have a more normal gastrointestinal function in the immediate post-surgical recovery period.

Medical personnel have used antacids and H2 blockers to neutralize the gastric acid which accumulates during delayed gastric emptying, but these treatments can incur a significant expense and do not efficiently remedy the underlying problem. Bowel stimulatory agents, such as metaclopramide, are often used but are not very effective.

Another possible avenue of treatment is direct treatment of the inactive organ system. Over the last century researchers have directed considerable effort towards the study of gastrointestinal motility. The duodenal bulb has been postulated to be the anatomic site of the duodenal pacemaker and as such would be the area responsible for generating activity fronts. Y. Ruckebusch and L. Bueno, *Gastroenterology*, 72:1309–14 (1977). The aboral propagation of activity fronts is known to be dependent on enteric cholinergic neurons. S. K. Sarna, et al., *Am. J. Physiol.*, 241:G16–23 (1981). The central nervous system does not initiate migrating motor complex ("MMC") activity in the intestines but does modulate this activity. In the human MMC, the site of initiation is not constant and may begin at sites other than the proximal bowel. MMC rapidly moves interdigestive contents down the small intestine thereby clearing the small intestine of residual food, secretions, and desquamated cells, preventing stagnation and bacterial growth. M. H. Sleisenger and J. S. Fordtran (eds.), *Gastrointestinal Disease: Pathophysiology, Diagnosis, Management*, Vol. II, "Movement of the Small and Large Intestine," 1088–1105 (1989).

Much of the interest in mechanisms of gastrointestinal motility stems from a desire to regulate intestinal motor activity in pathologic situations such as paralytic or adynamic ileus. Early treatments included the use of electric current as a regulator. F. Katona et al., *Wiener Klinische Wochenschrift*, 71:818 (1959) (hereinafter "Katona et al."). Subsequent studies of the adynamic gastrointestinal tract attempted to apply electrical stimuli that were strong enough to contract "paralytic" intestinal segments that retained reflex irritability. A. M. Bilgutay and C. W. Lillehei, *Ann. Surge*, 158:338 (1963); A. M. Bilgutay et al., *University of Minnesota Medical Bull.*, 36:70 (1964) (hereinafter "Bilgutay et al.").

Bilgutay et al. reported that electrical stimulation of the antrum in post-operative patients reduced the average time to first reported flatus from 55 hours to 20 hours. This desirable clinical effect, however, could not be confirmed in subsequent studies. D. C. Quast et al., *Surg. Gynec. Obstet*, 120:35–37 (1965); J. M. Moran and D. C. Nabseth, *Arch. Surg.*, 91:449–451 (1965); T. Berger et al., *Nord. Med.*, 74:1031 (1965); C. Wells et al., *Lancet*, I:4–10 (Jan. 4, 1964). In 1966 Sonneland concurred with other prominent investigators in the field that the electronic gastrointestinal pacemaker was of no value. J. Sonneland, *Am. J. Surg.*, 111:200–201 (1966).

In 1977 Gladen and Kelly reported that the canine gastric and intestinal pacesetter potentials were different as shown by electrical pacing. This finding helped to explain why electric stimulation of the gastric pacesetter would not regulate the intestinal pacesetter potential or alter intestinal movement. H. E. Gladden and K. A. Kelly, *Mayo Clin. Proc.*, 52:51–53 (1977). More recent attempts to electrically pace the human intestine post-operatively have likewise met with failure. Soper et al., *Surgery*, 107: 63–68 (1990), reported that electric pulses (50 msec, 5 to 15 mA, 11–13 cpm) did not alter or regulate the pattern of intestinal pacer potentials in any patient at any time after operation.

Clearly, there has been a long and unmet need for effective treatment of gastrointestinal disorders following surgery. In spite of numerous attempts to address this problem with direct electrical stimulation, the loss of normal gastrointestinal function following many surgical procedures remains a serious clinical problem.

The present inventors have discovered that chemical stimulation is an alternative to electrical stimulation for enhancing contractility in the adynamic gastrointestinal tract. Although local chemical stimulation of the gastrointestinal tract had not heretofore been used in an in vivo setting, certain chemicals have been shown to influence the motor activity of bowel tissues. The effect of muscarinic agonists such as acetylcholine on isolated intestinal smooth muscle preparations has been characterized. For example, concentrations of acetylcholine in the range of $10^{-6}$ to $10^{-8}$ g/ml have been shown to cause contraction of such ex vivo preparations. C. F. Code (Ed.) *Handbook of Physiology*, Vol. IV, "The Alimentary Canal, Motility," 2173–2187 (1968) (hereinafter "*Handbook of Physiology*"). In muscle preparations that spontaneously contract and relax, this activity is either made more frequent or is abolished and replaced by a steady high level contraction. Of note is the fact that depolarized smooth muscle contracts when exposed to acetylcholine. This suggests that neither the normal resting membrane potential nor the discharge of action potentials is required for the action of the agent, if the action sought is muscle contraction. *Handbook of Physiology*, 2173-2187.

The study of chemical action on intestinal smooth muscle is complicated by the presence of viable neurons even in isolated preparations. Consequently it can be difficult to determine whether the effect of a given chemical is the result of a direct effect on the smooth muscle or whether the effect is mediated by neuronal elements. Katona et al. Under normal conditions acetylcholine is released from certain nerve endings. If the concentration of the transmitter reaches a threshold level, depolarization of the muscle membrane occurs. *Handbook of Physiology*, 2173-2187.

Controlled release systems have distinct advantages over conventional drug therapies. Conventional systemic therapies go through a cycle in which the concentration of the drug steadily increases upon ingestion of the drug, peaks and subsequently declines over time. Each drug has an upper threshold over which the drug is toxic to the patient, and a lower threshold under which it is not effective. Repeated cycling can induce periods of alternating toxicity and ineffectiveness. Further, in conventional therapies, the therapeutic agent circulates through the patient's bloodstream, coming into contact with numerous organ systems. Often a high systemic dose is required so that the targeted organ system receives an adequate dose of the drug. An advantage, therefore, of a controlled, localized delivery system is that the drug is targeted to a selected organ system, thereby minimizing adverse side effects caused by either high systemic dosages or presence of the drug in other organs. Controlled drug release systems have been used to treat brain disorders, such as Parkinson's disease. U.S. Pat. No. 4,883,666.

For the purposes of drug delivery, selected drugs have been combined with biocompatible polymer matrices. For example, silicone elastomers may be used as permeant carriers. Their use in the health care field has increased in recent years because of the relative high permeability of silicone elastomers compared with other elastomers. The high rate of permeation is due to the flexible nature of siloxane polymer chains. This increased mobility effectively increases the usable volume of the polymer.

Several types of drug delivery systems using silicone elastomers have been described in the literature. The most commonly used method depends on release of drug through the walls of a hollow device, as in a capsule or tubing. P. J. Dzuik and B. Cook, *Endocrin.*, 28:208 (1966); S. J. Segal and H. Cook, 23rd Meeting of Amer. Fert. Soc., Apr. 14-16, 1967, Washington, D.C.; J. Folkman and V. H. Mark, *Trans. N.Y. Acad. Sci.*, 30:1187 (1968); E. R. Garrett and P. B. Chemburkar, *J.Pharm. Sci.*, 57:1401 (1968); F. A. Kind et al., *Acta Endo.*, 64:253 (1970); K. Sundaram and F. A. Kincl, *Steroids.* 12:517 (1968); H. Tatum, *Contracep.*, 1:253 (1970); W. E. Berndton et al., *Endocrin.*, 62:1 (1974).

A second type of drug delivery device consists of a mixture of silicone elastomer and the powdered form of a drug. The device is catalyzed and then cast into a desired shape. A number of drugs have been investigated in this regard and their release from the drug-polymer matrix documented. G. L. Neil et al., Chemother., 18:27 (1973); J. Folkman and D. M. Long Ann. N.Y. Acad. Sci., 111:857 (1964); H. Gottlieb et al., *Physiol. and Behavior*, 12:61 (1974); T. J. Rosman, *J.Pharm. Sci.*, 61:46 (1972); D. R. Mishell and M. E. Lumkin, *Fert. and Steril.*, 21:99 (1970). It is possible to determine the amount of drug present in the drug-polymer matrix. F. Theeuwes et al., *J.Pharm. Sci.*, 63:427 (1974). The method of Theeuwes et al. uses differential scanning calorimetry and provides information about drug-polymer interactions in addition to assaying the amount of drug present.

SUMMARY OF THE INVENTION

The present invention is a method and article of manufacture for the treatment of disorders associated with smooth muscle function in an organ. The invention is practiced by selecting at least one neuroactive substance that has a therapeutic effect on the smooth muscle disorder. Next, a controlled, localized delivery means is selected and the selected neuroactive substance and delivery means are combined to form a treatment element. Last, the treatment element is placed in contact with the organ of interest, initiating the therapeutic effect.

A variety of organs can be treated with such a treatment element including the gastrointestinal tract, urinary bladder, uterus, and body sphincters. Such a treatment element can have an ameliorative effect on an adynamic, hypodynamic, or hyperdynamic condition of the gastrointestinal tract. The means for controlled, localized delivery may be a biocompatible polymer matrix adapted for contact with such an organ. The neuroactive substance, e.g. a neurotransmitter such as acetylcholine, may be dispersed within the polymeric matrix. The shape and size of the drug/matrix element is pre-determined to maximize therapeutically useful contact with the organ. The treatment element can contact either the inside or outside of the organ or may be embedded within the organ tissue structure. With respect to the gastrointestinal tract, for example, the treatment element may be placed on the external serosal surface or on the luminal lining.

The present invention also includes an article of manufacture comprising packaging material and the treatment element within the packaging material, wherein the packaging material comprises a label that indicates that the treatment element can be used for treating a disorder associated with smooth muscle function in an organ.

BRIEF DESCRIPTION OF THE FIGURES

FIG. 1 depicts intraluminal pressure recordings from the guinea pig duodenum.

FIG. 2 depicts intraluminal pressure recordings from the guinea pig duodenum.

FIG. 3 depicts intraluminal pressure recordings from the cat duodenum.

FIG. 4 depicts electrical recordings from the guinea pig heart (upper-most tracing) and duodenum (lower-most tracing). FIG. 4C depicts return of the adynamic state following removal of the chemical pacemaker.

FIG. 5 depicts electrical recordings from the guinea pig heart (upper-most tracing) and duodenum (lower-most tracing).

DETAILED DESCRIPTION

Figure 1A:
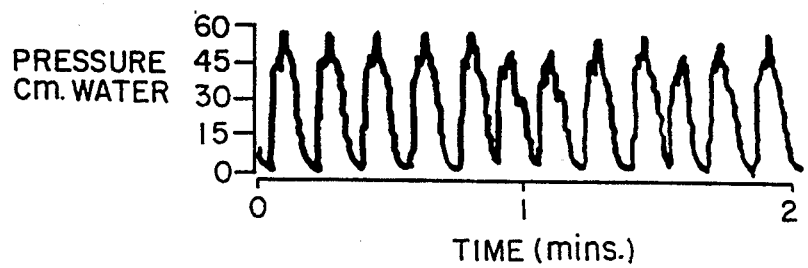
FIG. 1A depicts bowel activity immediately after laparotomy.

This invention utilizes controlled release systems that deliver drug dosages at a predetermined rate, for a limited period of time, to a delimited tissue area on or in an organ of interest. The rate of drug delivery is determined by the mechanism of the controlled release system and is relatively independent of the local microenvironment such as pH.

The method of the present invention involves the selection of a neuroactive agent and a means for controlled, localized delivery of the neuroactive agent to the targeted organ. The neuroactive substance is preferably a neurotransmitter, for example acetylcholine, methacholine, pilocarpine but does not exclude other neuroactive substances, e.g. barium chloride. The delivery means can be a biocompatible polymer matrix, preferably a silicone matrix. After combining the selected drugs with the biocompatible polymer matrix to form a treatment element, the element is solidified. As a result, the drug/matrix treatment element takes the form of the mold in which it hardened. By encasing all but one surface of the device with an impermeable, biocompatible substance, such as polyethylene, one can select the surface or surfaces from which drug release will occur. When applied to a moist surface, such as bowel, fluid enters the interstices of the matrix and solubilizes the drug. With additional fluid uptake, the drug is forced from the matrix and diffuses across the thin film of fluid at the device/bowel interface. High local concentrations are achieved without significantly affecting systemic concentrations.

In a preferred embodiment, the drug/matrix consists of a mixture of neuroactive substance in silicone elastomer (Dow Corning Corporation, Silastic ® MDX-4-4210). A preferred embodiment of the drug/matrix mixture consists of a concentration of about 8 to 30% by weight mixture of powdered neuroactive substance. A most preferred embodiment of the drug/matrix mixture comprises a concentration of about 15% by weight of powdered neuroactive substance. The powdered neuroactive substance may be any of a variety of selected neurotransmitters functional in a desired smooth muscle organ system, for example acetylcholine chloride (Sigma Chemical, Cat. No. A6625 and No. 420-150), acetyl-$\beta$-methacholine chloride (Sigma Chemical, Cat. No. A2251), pilocarpine hydrochloride (Sigma Chemical, Cat. No. P6503) or barium chloride (Sigma Chemical, Cat. No. B0750). The selected neuroactive substance is mixed with the base silicone elastomer prior to curing. The silicone elastomer is further prepared in accordance with recommended methods of the manufacturer (Dow Corning Corporation). The pacemaker may be cast in the shape of a rod, with each end of the rod having a surface area of approximately 1.0 mm$^2$ and 2.5 cm in length or other shape compatible with the anatomic properties of the organ of interest. It is then sealed along its length with polyethylene, leaving the silicone elastomer exposed at each end. The length, diameter and amount of exposed elastomer of the therapeutic treatment device may be varied depending on conditions. For example, the interstitial volume of polymer and the concentration of the neuroactive substance will vary depending on the desired local dosage.

An alternative embodiment of the localized, controlled delivery means may be a pump system that regulates the administration of the therapeutic agent. In a pump system, such as a syringe pump, the drug is delivered at a constant rate by a syringe barrel that moves at a constant speed.

The therapeutic treatment element is placed in contact with the target organ. This contact may be on inside or outside surfaces of the organ. Alternatively, the treatment element may be placed within the tissue structure of the organ, using standard tissue implant techniques. When the target organ is the intestinal tract, the preferred location for placing the treatment element is on the serosal surface of the proximal duodenum. The treatment element, however, may be placed at any point on or within the gastrointestinal tract, depending on the desired therapeutic effect. Further, more than one treatment element may be utilized to treat the smooth muscle disorder. In the case where the treatment element is being used to prevent or correct a post-surgery dysfunction, the treatment element preferably is placed inside the patient or subject organism at the time of the original surgery. Alternatively, the treatment element may be placed in the patient or subject organism by means of endoscopy.

For most human patients having abdominal surgery, the treatment element should contain sufficient drug so that the active ingredient continues to work for about three to five days. However, other time frames may be used as appropriate in particular clinical settings. The treatment device should remain inside the patient or subject organism during that period. The device need not remain directly affixed to the tissue structure of the dysfunctional organ, as long as the device maintains contact with some portion of the dissolving solution (e.g. moisture on the surface of an intestine). The treatment device can remain indefinitely inside the patient or subject organism, or may be removed by methods known to those having ordinary skill in the art.

This method for treating a disorder associated with smooth muscle function in an organ effectively starts peristaltic activity and increases such activity. The method may be adapted to regulate over-active organs through the application of appropriate counter-active agents.

The invention will be further understood with reference to the following illustrative embodiments, which are purely exemplary, and should not be taken as limiting the true scope of the present invention as described in the claims.

EXAMPLE 1

Preparation of Treatment Element

The treatment element, or chemical pacemaker, used in experiments comprised a mixture of powdered neuroactive substance and silicone elastomer. The neuroactive substances used in making treatment elements included acetylcholine chloride (Sigma Chemical Company, Cat. No. A6625 and No. 420-150), acetyl-β-methylcholine chloride (Sigma Chemical, Cat. No. A2251), pilocarpine hydrochloride (Sigma Chemical, Cat. No. P6503) and barium chloride (Sigma Chemical, Cat. No. B0750). Various concentrations of the powdered acetylcholine were tested including 8%, 11%, 15%, 20%, and 30% by weight. All of the different concentrations worked effectively. The higher concentrations worked more quickly than the lower ones. Methylcholine, pilocarpine and barium chloride were all tested at a concentration of 15% by weight. The powdered neuroactive substances were mixed with base elastomer (Dow Corning, Silastic® MDX-4-4210) prior to curing. The elastomer MDX-4-4210 is a room temperature vulcanizing elastomer that is clear in color prior to mixing with the powdered neuroactive substance.

Following mixing of the neuroactive substance and the silicone elastomer, the mixture was cured (solidified) using the procedures recommended by the manufacturer. A room temperature curing protocol (about 23° C. for approximately 24 hours) and higher temperature curing protocols (about 40° C. for approximately five hours and about 100° C. for approximately 15 minutes) were used with functionally similar results. The chemical pacemaker was cast in the shape of a rod approximately 2.5 cm in length and with each end of the rod having a surface area of approximately 1.0 mm$^2$. Each rod was sealed along its length with polyethylene, leaving the silicone elastomer exposed at each end. The polyethylene coating limited diffusion of acetylcholine out of the rod-shaped polymer matrix to a region of approximately 1.0 mm$^2$ of exposed elastomer matrix at each end of a rod.

EXAMPLE 2

Treatment of Adynamic Gastrointestinal Tract—Guinea Pig

Guinea pigs, 350–450 g, received food and water ad-libitum. All experiments were performed at the same time each morning. The animals were anesthetized with intraperitoneal injection of 40 mg/kg sodium pentobarbital. Following induction of anesthesia, a tracheotomy was performed and the animals were ventilated with room air.

For each anesthetized animal, a laparotomy was performed by opening the abdomen with a midline incision extending from the xiphoid process to the infraumbilical region. The proximal duodenum was intubated via passage of 14 G polyethylene tubing through an enterostomy placed in the antrum of the stomach. Once positioned, the tubing was secured by a ligature placed just proximal to the gastroduodenal junction. A second ligature was placed 3 cm distal to the first and the closed bowel loop inflated with normal saline solution to a pressure of approximately 10 cm of water. This pressure was recorded and balanced out, and used as an established baseline for subsequent treatment modalities. Pressure within the lumen of the bowel loop, i.e., intraluminal pressure, was measured with a Sorenson Transpac® II transducer and was recorded with a Gilson Strip Chart Recorder.

Following the above-referenced manipulation of the bowel, the loop of interest was left exposed on the abdomen in order to minimize cardiac and respiratory induced changes in intraluminal pressure. The entire abdomen was covered with clear plastic wrap to prevent drying. Normal saline solution at room temperature was used to periodically moisten the abdominal contents. Continuous recordings of intraluminal pressure and periodic measurements of extraluminal temperature were made throughout the procedures.

Over a period of 1–2 hours following surgical manipulation, the temperature of the exposed portion of the gastrointestinal tract was allowed to fall to a minimum temperature of 26° C. Over this time, the mechanical activity of the bowel decreased as evidenced by a decline in both "small wave" and "large wave" intraluminal pressure changes. Alternating contraction and relaxation by the circular muscles in the gastrointestinal tract correlate with small wave or "segmentation" motility. J. D. Wood, *Ann. Rev. Physiol.*, 43:33–51 at 44 (1981) (hereinafter "Wood"); A. C. Guyton, *Textbook of Medical Physiology*, "General Principles of Gastrointestinal Function—Motility, Nervous Control, and Blood Circulation," 688–697 (1991). The forces exerted by the circular muscles mix the intraluminal contents. Large wave motility, also called peristaltic motor pattern, relates to sequential contraction of the circular and longitudinal muscles along the intestinal tract. Wood at 46. Large wave motility propels the intraluminal contents along the intestine. The bowel was considered to be adynamic when large and small wave activity had ceased. When an adynamic condition had been achieved, a treatment element as described in Example 1 was contacted with the serosal surface of the exposed proximal duodenum. The treatment element was positioned over the exposed loop of interest such that the elastomer-exposed surface of one end was in contact with the serosal surface. The contact was such as to cause a slight inward deflection of the intestinal surface, and the treatment element was held in place with a clamp or by hand.

Figure 1B:
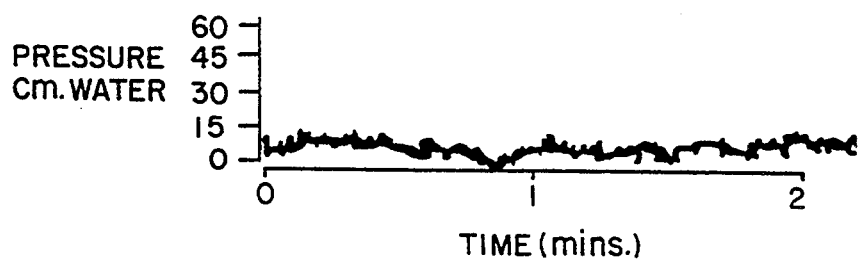
FIG. 1B depicts the loss of bowel activity occurring after manipulation and cooling.
Figure 1C:
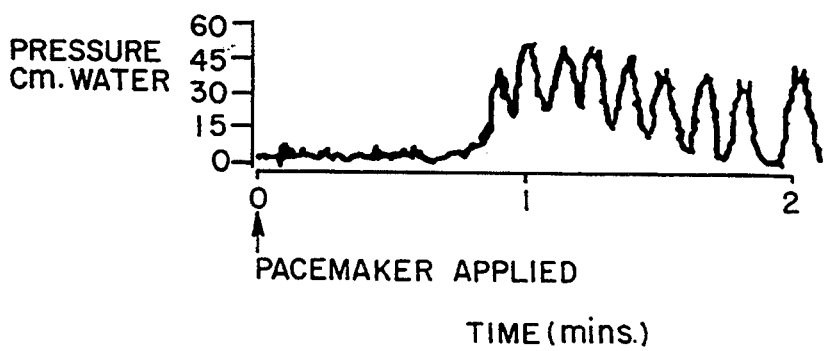
FIG. 1C depicts the return of bowel activity when the chemical pacemaker is applied to the adynamic bowel shown in FIG. 1B.
Figure 1D:
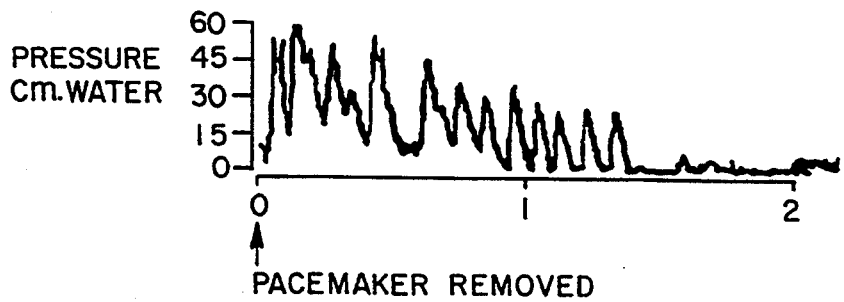
FIG. 1D depicts return of the adynamic state following removal of the chemical pacemaker.

Experiments were performed on a total of six guinea pigs. Application of the treatment element to the serosal surface consistently caused an increase in mechanical activity as measured by changes in intraluminal pressure. FIG. 1 depicts results from one of these experiments, in which the treatment element comprised 15% acetylcholine. In FIG. 1A, the intraluminal pressure of the guinea pig duodenum is recorded immediately following laparotomy. In FIG. 1B (90 minutes later), with the temperature adjacent to the bowel at 26° C., the bowel is considered to be adynamic. In FIG. 1C, application of the chemical pacemaker induces both a rise in the baseline pressure and a return of contractile activity. There was a delay of approximately 1 minute between pacemaker contact and return of contractile activity. Following removal of the pacemaker, baseline pressure and contractile activity returned to pre-contact levels, as depicted in FIG. 1D. The decline in activity to pre-contact levels occurred over approximately 1.5 minutes.

Application of a treatment element without acetylcholine loaded into the matrix produced no detectable effect on duodenal activity. Significantly, acetylcholine-loaded pacemakers, applied to the normoreactive bowel, had little effect on smooth muscle wave activity, although there was a small increase in the baseline intraluminal pressure (not shown).

EXAMPLE 3

Treatment of Hypodynamic Gastrointestinal Tract—Guinea Pig

Figure 2A:
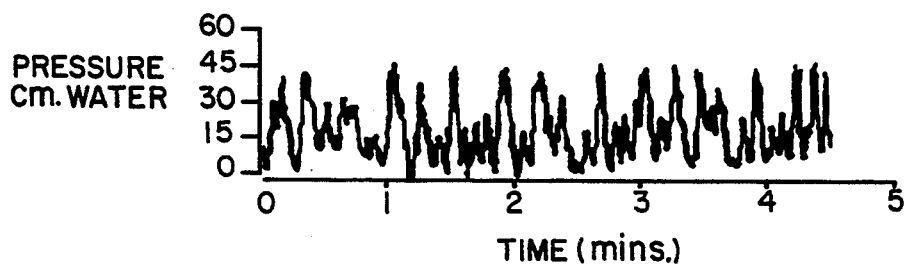
FIG. 2A depicts bowel activity immediately after laparotomy.
Figure 2B:
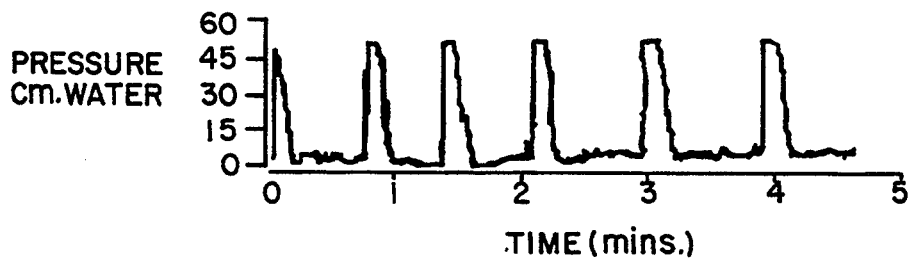
FIG. 2B depicts the slowing of bowel activity occurring after manipulation and cooling. This hypodynamic state precedes the adynamic state.
Figure 2C:
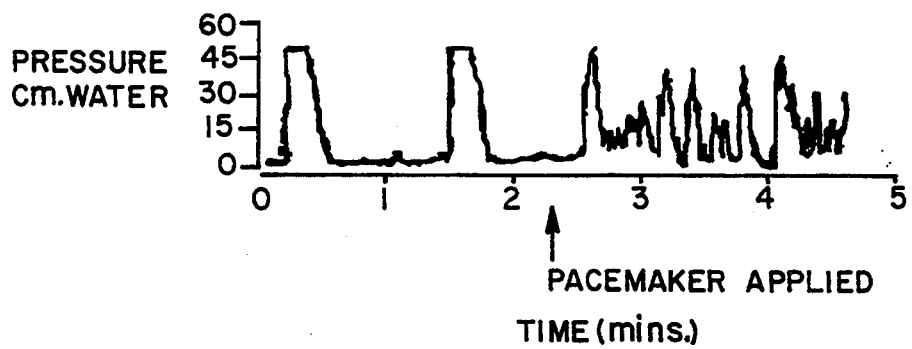
FIG. 2C depicts the return of bowel activity with the application of the chemical pacemaker.
Figure 2D:
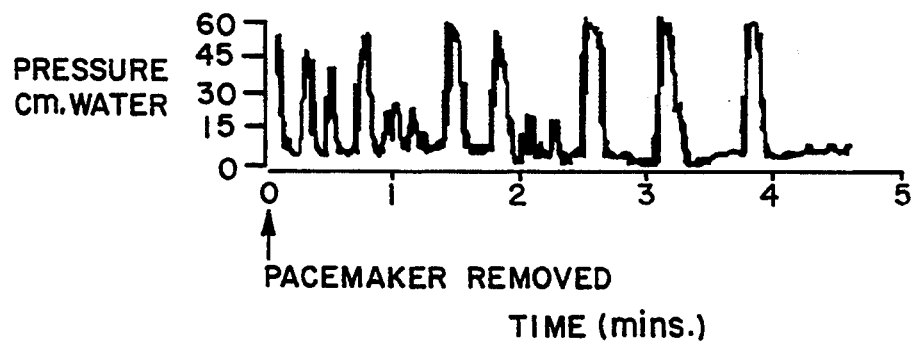
FIG. 2D depicts return of the hypodynamic state following removal of the chemical pacemaker.

Experimental procedures were as described in Example 2, above, except that the bowel was treated in a hypodynamic rather than an adynamic condition. The hypodynamic condition is defined as measurable activity of less than one wave per minute. A response similar to the adynamic bowel is documented in FIG. 2. FIG. 2A depicts the duodenal smooth muscle activity of a guinea pig immediately following laparotomy. The pressure recordings depicted in FIG. 2B reflect a relatively hypodynamic state compared to the control. Application of the chemical pacemaker (15% acetylcholine) returned the bowel mechanical activity to near normal levels, as documented in FIG. 2C. As depicted in FIG. 2D, removal of the device allowed the duodenum to return to its hypodynamic state.

EXAMPLE 4

Treatment of Adynamic Gastrointestinal Tract—Cat and Dog

Figure 3A:
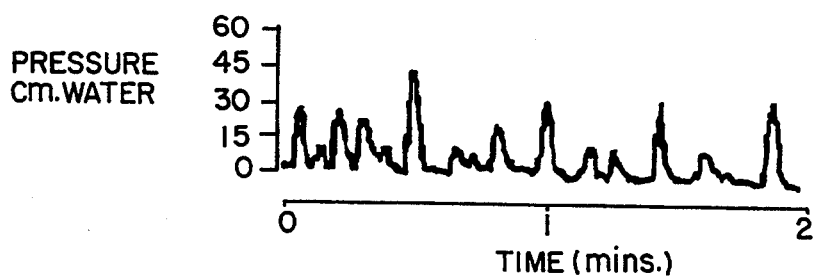
FIG. 3A depicts bowel activity immediately after laparotomy.
Figure 3B:
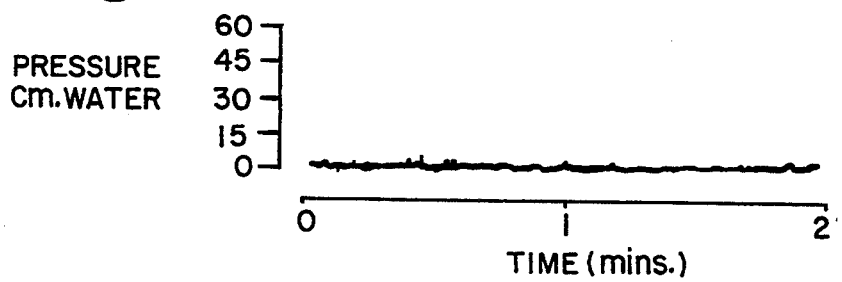
FIG. 3B depicts the loss of bowel activity occurring after manipulation and cooling.
Figure 3C:
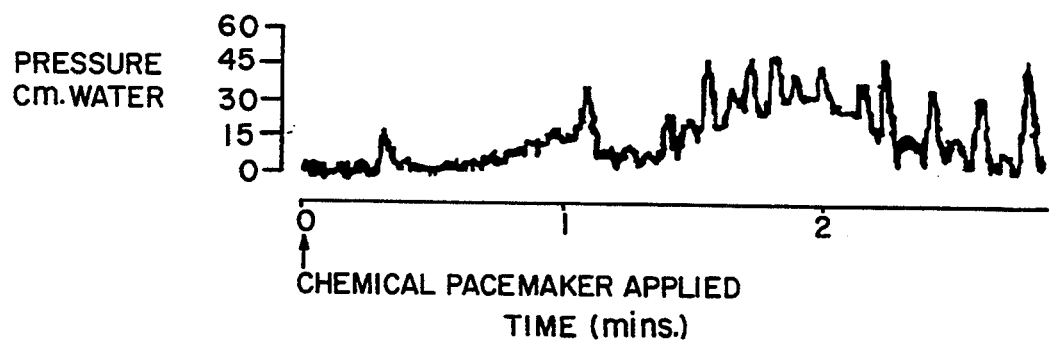
FIG. 3C depicts the return of bowel activity when the chemical pacemaker is applied to the adynamic bowel shown in FIG. 3B.
Figure 3D:
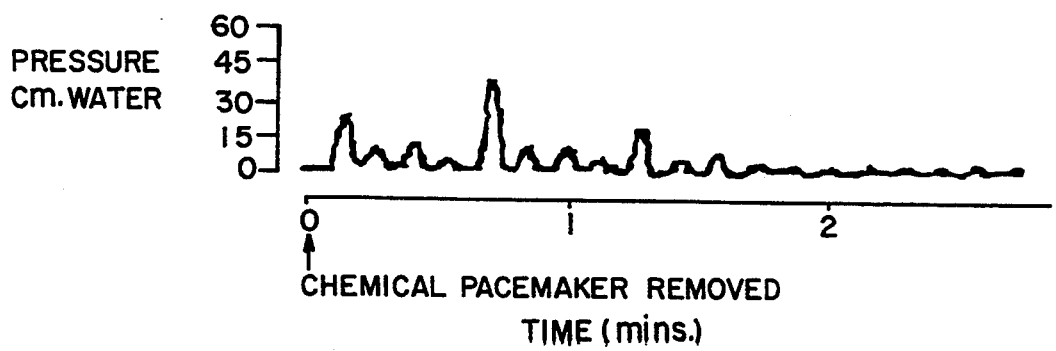
FIG. 3D depicts return of the adynamic state following removal of the chemical pacemaker.

The acetylcholine chemical pacemaker predictably was found to have a comparable effect on the intestines of other mammalian species. Such comparable effect in other mammals is expected due to the well-known functional similarity of neurotransmitter action in mammals and other vertebrates. FIG. 3 documents that the adynamic bowel of the cat responds in a manner comparable to the adynamic bowel of the guinea pig. In FIG. 3A, the intraluminal pressure of the cat duodenum is recorded immediately following laparotomy. FIG. 3B depicts the loss of bowel activity that occurs after manipulation and cooling. In FIG. 3C, application of the chemical pacemaker induces both a rise in the baseline pressure and a return of contractile activity. Following removal of the pacemaker, baseline pressure and contractile activity returned to pre-contact levels, as depicted in FIG. 3D. In comparison to the results obtained with the guinea pig, there was a longer delay between application and removal of the pacemaker and the resulting effect, as can be seen in FIG. 3. Nevertheless, application of the chemical pacemaker restored activity to the adynamic bowel of the cat as it had restored activity to the adynamic bowel of the guinea pig. Experiments on three dogs using the above-described procedures yielded qualitatively similar results to those seen with the guinea pig and cat.

EXAMPLE 5

Electrical Recordings—Guinea Pig

Figure 4A:
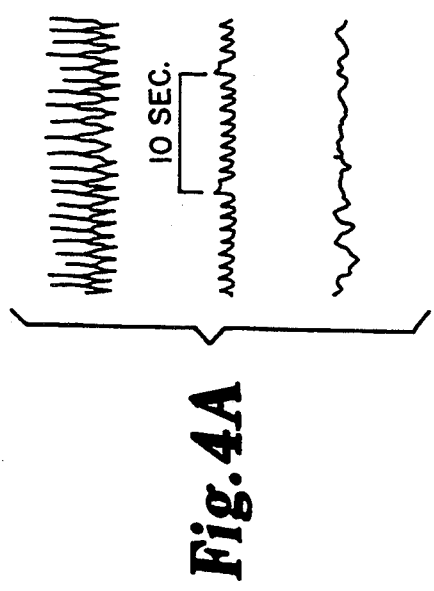
FIG. 4A depicts the activity of the adynamic bowel.
Figure 4B:
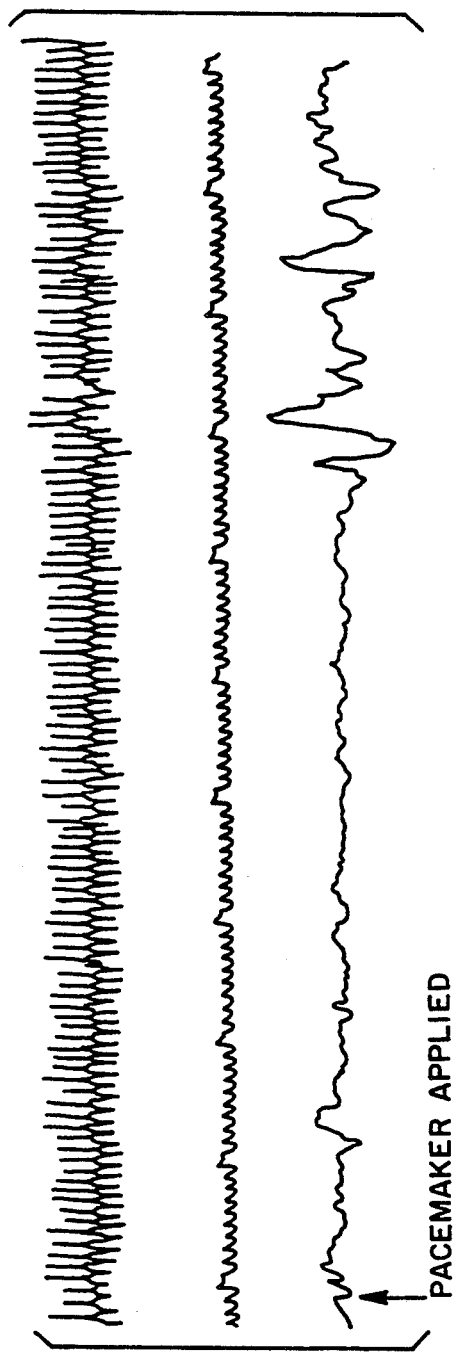
FIG. 4B depicts the increased electrical activity following application of the chemical pacemaker.

The procedures set out in Example 2, above, were repeated except that electrical activity, rather than intraluminal pressure, was recorded from the guinea pig bowel. Two bipolar, insulated stainless steel electrodes with the tips exposed were impaled into the wall of the exposed intestinal loop (proximal duodenum). The electrodes were separated by a distance of approximately 2.0 mm and were connected to a standard chart recorder for recording during the various treatment phases. At the same time, recordings of heart electrical activity of the same animal were made in order to monitor the systemic effects deriving from local administration of neurotransmitter to the gastrointestinal tract. FIG. 4 documents the electrical activity of the heart and exposed loop following induction of an adynamic condition in the loop. The upper tracings in FIG. 4 record the heart beat and the lower tracings record the electrical activity of the exposed intestinal loop with attached electrodes. The middle tracings represent timed intervals as indicated in the Figure. FIG. 4A depicts the baseline activity of the adynamic guinea pig bowel. FIG. 4B documents an increase in intestinal electrical activity upon application of the acetylcholine pacemaker. FIG. 4C demonstrates the return of electrical activity to the adynamic condition upon removal of the chemical pacemaker.

Thus, the pattern of electrical activity parallels the pattern of mechanical activity seen during and after application of the chemical pacemaker. Moreover, as can be seen in FIG. 4, the heart rate is not significantly affected by this local application of a chemical pacemaker. Therefore, the primary effect of the neurotransmitter is confined to the organ of interest, as would be desired in a clinical setting.

EXAMPLE 6

Interior Placement of the Chemical Pacemaker

Guinea pigs were prepared as described in Examples 2 and 3, above. Two bipolar, insulated stainless steel electrodes with the tips exposed were impaled into the wall of the exposed duodenal loop approximately 2.0 mm apart. Then, an incision through the wall of the intestinal loop and into the luminal cavity was made approximately 2-3 cm distal from the electrodes. Upon attainment of the hypodynamic State (less than one measurable wave per minute), a pacemaker with 15% acetylcholine as described in Example 1, above, was inserted into the incision. One end of the pacemaker remained external to the outer serosal surface and was clamped or manually held for positioning. The other end was moved to a position near the electrode emplacement and held against the wall of the lumen. The position of the interior end of the pacemaker was externally observable due to a slight outward deflection of the outer surface of the bowel deriving from the contact of the pacemaker with the interior luminal surface.

Figure 5A:
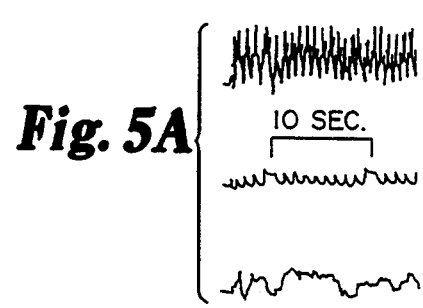
FIG. 5A depicts the activity of the adynamic bowel.
Figure 5B:
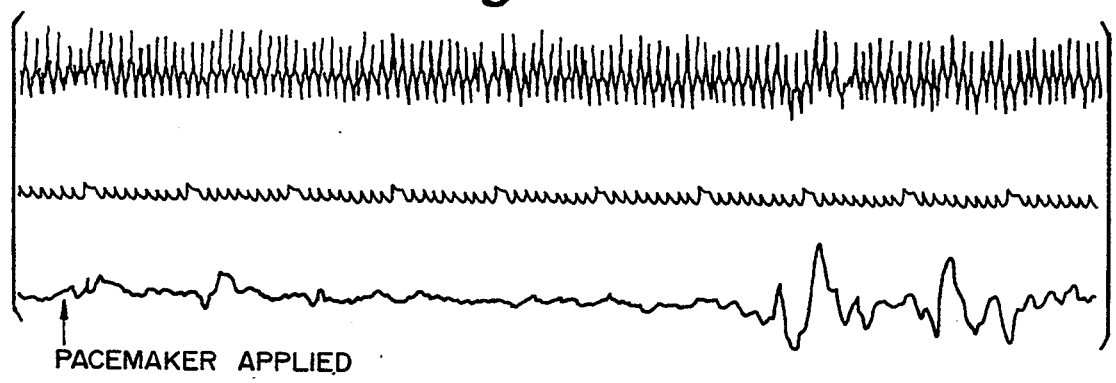
FIG. 5B depicts the increased electrical activity following application of the chemical pacemaker to the inside of the duodenum.
Figure 5C:
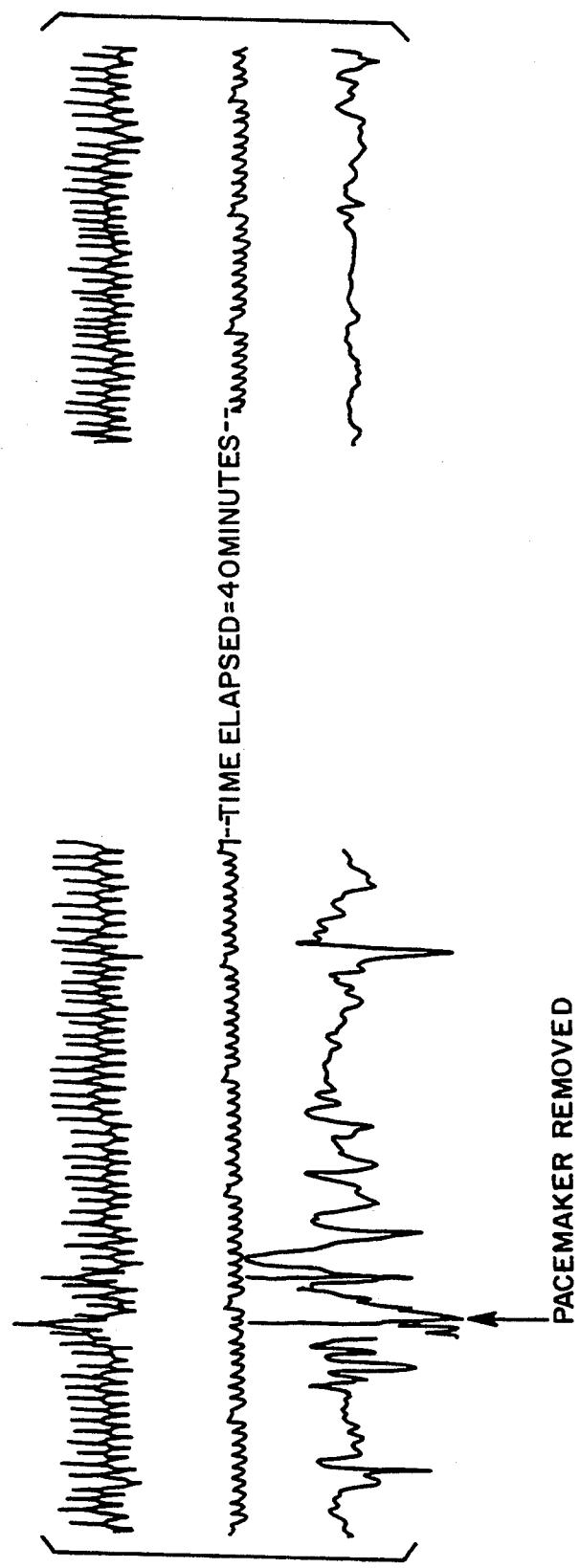
FIG. 5C depicts return of the adynamic state following removal of the chemical pacemaker.

The pacemaker was held in this position until a definite increase in small or large wave frequency was noted. The device was then removed by pulling it out through the incision. Application of the chemical pacemaker to the interior of the intestine caused an increase in electrical activity in two of four guinea pigs tested. Results in the remaining two guinea pigs were marginal, possibly due to sub-optimal contact of the chemical pacemaker with the luminal wall. Nevertheless, these experiments clearly demonstrate the ability of an internally placed chemical pacemaker to increase the electrical activity of the bowel. As with the above-described experiments in Example 5, the heart rate was not significantly affected by this local administration of acetylcholine to the bowel. Positive results obtained with one of the above-described guinea pigs are documented in FIG. 5.

The foregoing detailed description has been provided for a better understanding of the invention only and no unnecessary limitation should be understood therefrom as some modifications will be apparent to those skilled in the art without deviating from the spirit and scope of the appended claims.

We claim:

1. A method for treating a disorder associated with smooth muscle function in an organ peripheral to the central nervous system, comprising:
   (a) selecting at least one neuroactive substance having a therapeutic effect on said disorder;
   (b) selecting means for controlled, localized delivery of said substance to said organ;
   (c) combining said at least one neuroactive substance with said means for controlled, localized delivery to form a treatment element; and
   (d) attaching said treatment element to a selected portion of the serosa of said organ in a manner to accomplish said therapeutic effect.

2. The method of claim 1, wherein said organ is a mammalian gastrointestinal tract.

3. The method of claim 1, wherein said organ is a mammalian intestinal tract.

4. The method of claim 3, wherein said mammalian intestinal tract is a human intestinal tract.

5. The method of claim 1, wherein said organ is a urinary bladder.

6. The method of claim 1, wherein said organ is a uterus.

7. The method of claim 1, wherein said organ is a body sphincter.

8. The method of claim 2, wherein said disorder is an adynamic condition of said gastrointestinal tract.

9. The method of claim 2, wherein said disorder is a hypodynamic condition of said gastrointestinal tract.

10. The method of claim 2, wherein said disorder is a hyperdynamic condition of said gastrointestinal tract.

11. The method of claim 2, wherein said neuroactive substance is barium chloride.

12. The method of claim 2, wherein said neuroactive substance is a neurotransmitter.

13. The method of claim 12, wherein said neurotransmitter is selected from the group consisting of acetylcholine, methacholine, and pilocarpine.

14. The method of claim 13, wherein said neurotransmitter is acetylcholine.

15. The method of claim 1 wherein said means for controlled, localized delivery comprises a biocompatible polymer matrix adapted for contact with said organ.

16. The method of claim 15 wherein said treatment element comprises said neuroactive substance in combination with said polymer matrix, said neuroactive substance being dispersed within said matrix, said matrix having a shape and a size adapted for therapeutically useful contact with said organ.

17. The method of claim 16 wherein said contact is with a mammalian gastrointestinal tract.

* * * * *